United States Patent
Mori et al.

(10) Patent No.: US 8,076,368 B2
(45) Date of Patent: Dec. 13, 2011

(54) PERCUTANEOUS ABSORPTION TYPE CEREBRAL PROTECTIVE AGENT

(75) Inventors: Jun Mori, Toyama (JP); Tamaki Horiuchi, Toyama (JP); Seijiro Yama, Toyama (JP); Hitomi Waki, Toyama (JP); Shingo Shimada, Toyama (JP); Hitomi Hashitani, Toyama (JP)

(73) Assignee: Lead Chemical Co., Ltd,, Toyama (JP)

( * ) Notice: Subject to any disclaimer, the term of this patent is extended or adjusted under 35 U.S.C. 154(b) by 969 days.

(21) Appl. No.: 10/579,055

(22) PCT Filed: Nov. 12, 2003

(86) PCT No.: PCT/JP03/14362
§ 371 (c)(1),
(2), (4) Date: May 11, 2006

(87) PCT Pub. No.: WO2005/046680
PCT Pub. Date: May 26, 2005

(65) Prior Publication Data
US 2007/0148217 A1    Jun. 28, 2007

(51) Int. Cl.
*A61K 21/4152* (2006.01)
(52) U.S. Cl. ...................................... 514/404
(58) Field of Classification Search .................. None
See application file for complete search history.

(56) References Cited

U.S. PATENT DOCUMENTS 4,857,542 A    8/1989 Nishi et al.

FOREIGN PATENT DOCUMENTS

| EP | 0 208 874 A1 | 1/1987 |
|---|---|---|
| EP | 0 739 626 A2 | 10/1996 |
| EP | 0 947 584 A1 | 10/1999 |
| EP | 0 974 350 A1 * | 1/2000 |
| EP | 1 174 132 A1 | 1/2002 |
| EP | 1 559 426 A1 | 8/2005 |
| GB | 2 302 651 A | 1/1997 |
| JP | A 61-263917 | 11/1986 |
| JP | A 62-108814 | 5/1987 |
| JP | A 63-203613 | 8/1988 |
| JP | A 03-215425 | 9/1991 |
| JP | A 03-215426 | 9/1991 |
| JP | A 07-025765 | 1/1995 |
| JP | A 07-048250 | 2/1995 |
| JP | A 09-052831 | 2/1997 |
| JP | 10-265373 | * 10/1998 |
| JP | A 10-279480 | 10/1998 |
| WO | WO 02/34264 A1 | 5/2002 |
| WO | WO 03/024446 A1 | 3/2003 |

OTHER PUBLICATIONS

Masahiko Tanaka, "Pharmacological and Clinical Profile of the Free Radical Scavenger Edaravone as a Neuroprotective Agent", Abstract from Folia Pharmacologica Japonica, vol. 119 (2002), No. 5, 301-308.

* cited by examiner

*Primary Examiner* — James D Anderson
(74) *Attorney, Agent, or Firm* — Oliff & Berridge, PLC

(57) ABSTRACT

A percutaneous absorption type cerebral protective agent containing as an active ingredient, 0.1 to 30 percent by mass of 3-methyl-1-phenyl-2-pyrazolin-5-one represented by the following formula:

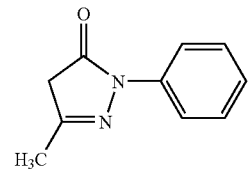

or a medically acceptable salt thereof in a base; a use of the compound as an active ingredient for the manufacture of a percutaneous absorption type pharmaceutical composition for protecting brain; and a method of protecting brain comprising administering to a patient the pharmaceutical composition as an active ingredient.

12 Claims, 2 Drawing Sheets

PERCUTANEOUS ABSORPTION TYPE CEREBRAL PROTECTIVE AGENT

FIELD OF THE INVENTON

The present invention relates to a medical agent that can prevent cerebral function against overall cerebral dysfunction including cerebral infarction and subarachnoid hemorrhage and the like, and in particular a percutaneous absorption type cerebral protective agent containing 3-methyl-1-phenyl-2-pyrazolin-5one as an active ingredient.

BACKGROUND OF THE INVENION

3-Methyl-1-phenyl-2-pyrazolin-5-one is a cerebral protective agent which has a free radical eliminating function and is used with an injectable solution (intravenous drip infusion; intravenous injection by drip) as an improving drug for neurological syndromes, impairment of daily living activities, and functional impairment in humans accompanied by cerebral infarction acute period. Recently, many people are suffering from cerebral dysfunction brought on by aging, variation in diet, an increase in stress in daily life, and the like, and as a result, quick and precise countermeasures for cerebral dysfunction are now an important issue in medicine.

Free radicals such as hydroxy radicals (—OH) which are produced in excess in the body during ischemia due to cerebral infarction or the like and after restoration of blood flow thereafter result in a chain reaction of oxygenation damage in cell membranes in humans, thereby further worsening cerebral ischemia damage. In this case, if an injectable solution containing 3-methyl-1-phenyl-2-pyrazolin-5-one (trade name: Radicut Injection 30 mg; injectable solution including 30 mg of active ingredient per dose) is used through intravenous drip infusion, the injectable solution demonstrates excellent treatment effects against cerebral ischemia damage by eliminating the hydroxy radicals in the bodies of humans.

The injectable solution, however, causes a patient pain due to the fact that an injection needle punctures the body (vein) of the patient during intravenous drip infusion of the injectable solution. Further, the intravenous drip infusion is normally performed on a patient who is lying down on a bed, which means the patient is restricted to the bed for a certain period of tie (i.e., while the intravenous drip infusion is being performed). In addition, with the exception of some injectable solutions such as insulin and interferon, injections are not able to be administered by the patient him/herself. An intravenous drip infusion of the injectable solution containing 3-methyl-1-phenyl-2-pyrazolin-5-one is also obviously not able to be administered by the patient him/herself, which means that (administration of) the intravenous drip infusion must be done by a doctor, a female nurse, or a male nurse. As a result, the patient is compelled to be admitted into a hospital or go to a hospital for the intravenous drip infusion. Even if the patient is admitted into a hospital or goes to a hospital for the intravenous drip infusion, the patient feels pain during the intravenous drip infusion, and a healthcare practitioner such as a doctor, female nurse, or male nurse must take the time to perform (administer) the intravenous drip infusion. As a result, if the intravenous drip infusion is administered twice daily according to the dosage regimen, for example, each time it causes the patient pain and takes the time of a healthcare practitioner.

Also, side-effects such as impaired liver function are being reported following intravenous drip infusion of the injectable solution. A temporary increase in the concentration of medication in the blood from the intravenous drip infusion can easily be assumed to be one cause. Given these circumstances, development of a preparation containing 3-methyl-1-phenyl-2-pyrazolin-5-one which is easy to administer, which has lasting effects over an extended period of time, and which has few side-effects is required.

When 3-methyl-1-phenyl-2-pyrazolin-5-one is used as an agent to normalize brain function, methods of administration as an injectable solution, an oral agent, or a suppository (administered rectally) are disclosed in Japanese Patent Application Laid-Open No. 61-263917, for example, but only an injectable solution is currently used in clinical practice. One reason for this is because many disorders that the agent to normalize brain function is aimed to treat occur following cerebral infarction, so many patients to whom the agent to normalize brain function is administered are incapacitated or unconscious which makes it difficult to administer the agent orally. In addition, many of the patients to whom the agent to normalize brain function is administered are elderly patients who fundamentally have a difficult time taking medication orally.

Furthermore, 3-methyl-1-phenyl-2-pyrazolin-5-one is quickly metabolized in the liver by glucuronate conjugation or sulfate conjugation so the effectiveness from the first passage effect in the liver is extremely low when administered orally. Also, 3-methyl-1-phenyl-2-pyrazolin-5-one is disclosed as a lipid peroxide production inhibiting agent (see Japanese Patent Application Laid-Open No. 62-108814, for example), an antiulcer agent (see Japanese Patent Application Laid-Open No. 3-215425, for example), an anti-hyperglycemic agent (see Japanese Patent Application Laid-Open No. 3-215426, for example), an agent for ocular disease (see Japanese Patent Application Laid-Open No. 7-25765, for example), an agent for treating/preventing acute hepatic failure (see Japanese Patent Application Laid-Open No. 9-52831, for example), and the like. All of these agents, however, are administered orally, intravenously, or rectally and thus have the drawbacks described above in clinical practice.

DISCLOSURE OF THE INVENTON

In view of the current situation, the inventors have achieved an invention of a cerebral protective agent containing 3-methyl-1-phenyl-2-pyrazolin-5-one which has a medicinal effect equal to, or greater than, the medicinal effect of 3-methyl-1-phenyl-2-pyrazolin-5--one when used as an injectable solution, and which solves the problems of the related art by employing a form of the percutaneous absorption preparation (also including a form of percutaneous absorption adhesive preparation) as a form of preparation instead of an injectable solution, as a result of intensive study of other methods of administration, aside from the foregoing method of administration, for 3-methyl-1-phenyl-2-pyrazolin-5-one.

Therefore, the present invention relates to a percutaneous absorption type ischemic cerebral protective agent characterized by containing as an active ingredient, 0.1 to 30 percent by mass of 3-methyl-1-phenyl-2-pyrazolin-5-one represented by the following formula:

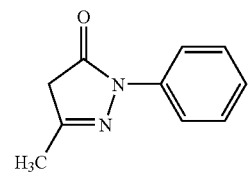

or a medically acceptable salt thereof in a base.

Also, the present invention relates to a use of 3-methyl-1-phenyl-2-pyrazolin-5-one resented by the following formula:

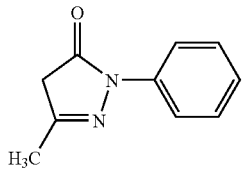

or a medically acceptable salt thereof in an amount of 0.1 to 30 percent by mass in a base, as an active ingredient for the manufacture of a percutaneous absorption type pharmaceutical composition for protecting brain.

Further, the present invention relates to a method of protecting brain comprising:
administering to a patient a percutaneous absorption type pharmaceutical composition that comprises, as an active ingredient, 3-methyl-1-phenyl-2-pyrazolin-5-one resented by the following formula:

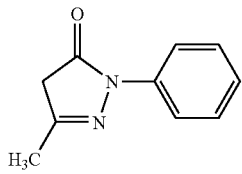

or a medically acceptable salt thereof in an amount of 0.1 to 30 percent by mass in a base.

Particularly preferable embodiments of the present invention are as follows.

The agent, use or method in which the base is an aqueous base:

The agent use or method in which the aqueous base contains, based on a total amount of the aqueous base, 1 to 20 percent by mass of a water-soluble polymer, 0.01 to 20 percent by mass of a cross-linking agent, 10 to 80 percent by mass of polyhydric alcohol, and 1 to 80 percent by mass of water:

The agent, use or method in which the base is a rubber base: and

The agent, use or method in which the rubber base contains, based on the total amount of the rubber base, 10 to 50 percent by mass of a rubber polymer, 10 to 50 percent by mass of a plasticizer, and 5 to 50 percent by mass of a tackifier.

The present invention has the following advantages.

a) The present invention is able to inhibit cerebral cell death that occur following ischemia, and additionally it makes possible to maintain an effective concentration of 3-methyl-1-phenyl-2-pyrazolin-5-one in the blood over an extended period of time.

b) In the present invention, it is easy to administer, as well as stop the administration of the agent. For example, when there are side effects from the agent, administration of the agent can be discontinued simply by wiping off the preparation (when it is in the form of an ointment for example), or removing the preparation (when it is in the form of an adhesive preparation, for example).

c) Because an effective concentration of the agent is able to be maintained in the blood over an extended period of time when the preparation is used once, the number of times the medication is administered can be reduced compared with the conventional intravenous drip infusion. As a result, it is possible to promote patient compliance and reduce the load on the caretaker during treatment.

d) While the preparation is being used, the concentration of the medication in the blood is maintained within a predetermined range so the concentration of the medication in the blood will not temporarily increase to an undesirable value as is the case with the intravenous drip infusion. Accordingly, it is possible to avoid the side-effects from the medication which accompany a temporary increase in the concentration of the medication in the blood.

BRIEF DESCRIPTON OF THE DRAWINGS

BEST MODE FOR CARRYING OUT THE INVENION

Figure 1:
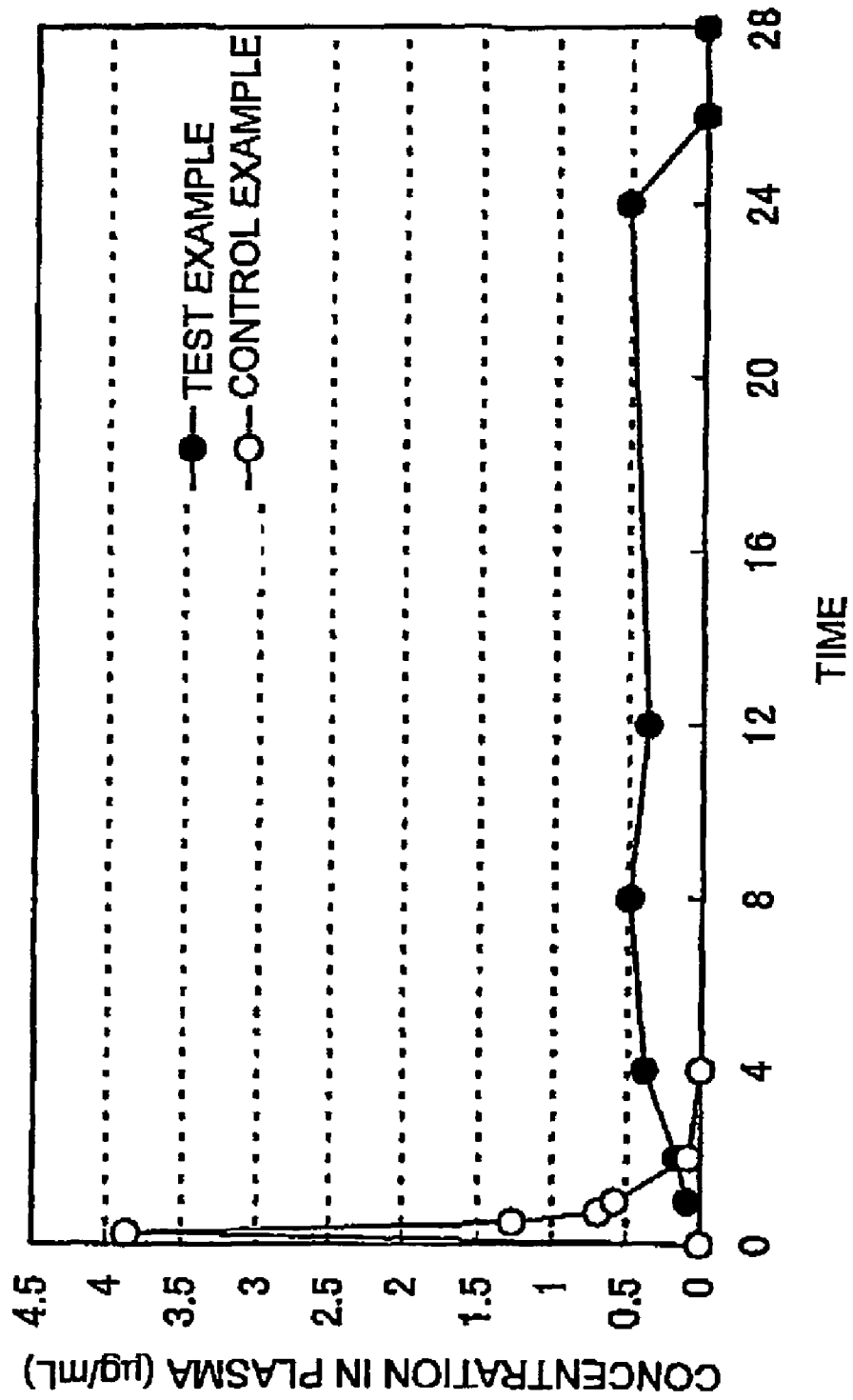
FIG. 1 is a graph showing the change of the concentration in rat plasma of 3-methyl-1-phenyl-2-pyrazolin-5-one in a case where the percutaneous absorption preparation of Example 1 has been applied to a rat or in a case where Radicut Injection has been intravenously administered to a rat.

Hereinafter, the present invention will be described in detail.

It is known that 3-methyl-1-phenyl-2-pyrazolin-5-one, which is the active ingredient of the present invention, has free radical eliminating function, for example eliminates hydroxy radicals (—OH) or the like to inhibit oxidation damage in cell membranes or the like. In the present invention, the blended amount of the active ingredient differs according to the formula, but it is desirable that 0.1 to 30 percent by mass, and more preferably 0.5 to 20 percent by mass, in particular 0.5 to 10 percent by mass, based on the total amount of base, be blended in a suitable base.

The pharmaceutical composition of the present invention may be in various suitable forms, for example, a solution, a slurry, an ointment, a paste, rubber, or the like, and can be manufactured as it is or in a more suitable form.

If the pharmaceutical composition of the present invention is used in the form of an adhesive preparation, it can be applied to the skin in that form which makes it convenient and easy to use. The adhesive preparation may also be in various adhesive preparation forms such as, for example, an adhesive skin patch, a plaster agent, a tape agent, or the like, depending on the use. The adhesive preparation can be manufactured by, for example, adding a predetermined amount of 3-methyl-1-phenyl-2-pyrazolin-5-one in a form suitable for coating (such as ointment form) to a suitable base (such as an aqueous base or a rubber base), applying this at a predetermined thickness to a suitable support medium, covering it from above with a liner, and cutting it to the desired size. The adhesive preparation may also be formed by first coating a liner with a base containing 3-methyl-1-phenyl-2-pyrazolin-5-one to form a base layer, covering this from above with a support medium, and then transferring the base layer onto the support medium.

It is preferable that the base in the pharmaceutical composition of the present invention is an aqueous base or a rubber base. As the aqueous base or the rubber base, an aqueous base made of a mixture of the following components, for example, can be used:

Aqueous base
Component 1): water-soluble polymer:
Component 2): cross-linking agent: and
Component 3): polyhydric alcohol, and
Rubber base
Component 4): rubber polymer:
Component 5): plasticizer: and
Component 6): tackifier.

The components 1) to 6) will be hereinafter be described.

Examples of the water-soluble polymer of component 1) include polyacrylic acid, polyacrylate, polyacrylic acid moiety neutralizer, polyacrylamide, polyethylene imine, polyvinyl alcohol, polyvinylpyrrolidone, carboxy vinyl polymer, methylcellulose, carboxymethylcellulose, carboxymethylcellulose sodium, hydroxyethylcellulose, starch acrylate, ethyl vinyl acetate, gelatin, starch, Eudragid, alginic acid, sodium alginate, tragacanth, and the like. Only one type of water-soluble polymer may be used or two or more types of water-soluble polymers may be suitably mixed together at a predetermined ratio and used. The compound content of the water-soluble polymer is 1 to 20 percent by mass, and preferably 3 to 6 percent by mass, based on the total amount of the water-soluble base.

As the cross-linking agent of component 2), for example, salts can be used which produce bivalent or trivalent metal ions when dissolved in water or the like. Examples of the cross-linking agent include hydroxides such as aluminum hydroxide and magnesium aluminum hydroxide, or inorganic acid or organic acid salts such as aluminum chloride, aluminum sulfate, dihydroxyaluminum aminoacetate, kaolin, aluminum stearate, magnesium hydroxide, magnesium chloride, and magnesium sulfate, or basic salts thereof, double salts such as aluminum alum, an aluminate such as sodium aluminate, inorganic aluminum complex salt and organic aluminum chelate compound, synthetic hydrotalcite, magnesium aluminometasilicate, magnesium aluminosilicate, aluminum nitrate, aluminum sulfate, EDTA-aluminum, aluminum allantoinate, aluminum acetate aluminum glycinal and the like. Only one type of cross-linking agent may be used or two or more types of cross-linking agents may be suitably mixed together at a predetermined ratio and used. The compound content of the cross-linking agent is 0.01 to 20 percent by mass, and more preferably 0.1 to 10 percent by mass, based on the total amount of the water-soluble base.

The salts that produce bivalent or trivalent metal ions and which serve as the cross-linking agent may be readily soluble in water or may be very insoluble in water. When an aluminum compound that is very insoluble in water is used as the cross-linking agent, a reaction speed adjuster can be added to the reaction system in order to facilitate gelatinization. In particular, the addition of acid makes it possible to increase the reaction speed of the gelatinization. The gelatinization speeds up remarkably by adding an organic acid that includes a hydroxyl group or a salt thereof, in particular, as the acid. Examples of the reaction speed adjuster include organic bases, organic acid salts, and organic acids having a chelate forming ability or coordinating property with respect to metal ions, such as citric acid, lactic acid, tataric acid, gluconic acid, glycolic acid, malic acid, fumaric acid, meta sulfonic acid, maleic acid, acetic acid, EDTA di sodium, urea, triethylamine, ammonia, and inorganic acids such as hydrochloric acid, phosphoric acid, sulfuric acids nitric acid and hydrobromic acid.

Examples of the polyhydric alcohol of component 3) include ethylene glycol, propylene glycol, trimethylene glycol, 1,3-butanediol, ethylene glycol monobutyl ether, triethyleneglycol, 1,4-butanediol, glycerin, trioxyisobutane, erythritol, pentaerythritol, xylitol, adonite, arodulcite, sorbitol, sorbit solution, mannitol, and polyethyleneglycol. Only one type of polyhydric alcohol may be used or two or more types of polyhydric alcohols may be suitably mixed together at a predetermined ratio and used. The compound content of the polyhydric alcohol is 10 to 80 percent by mass, and more preferably 10 to 60 percent by mass, based on the total amount of the base.

Examples of the rubber polymer of component 4) include a styrene-isoprene-styrene block copolymer, a styrene butadiene block copolymer, polyisobutylene, crude caoutchouc, polyisoprene, polybutene and the like. Only one type of rubber polymer may be used or two or more types of rubber polymers may be suitably mixed together at a predetermined ratio and used. The compound content of the rubber polymer is 10 to 70 percent by mass, and more preferably 20 to 50 percent by mass, based on the total amount of the base.

Examples of the plasticizer of component 5) include liquid paraffin, vegetable oil, animal oil, polybutene, low-molecular weight polyisobutylene, petrolatum, lanoline, premium aliphatic ester, and the like. Only one type of plasticizer may be used or two or more types of plasticizers may be suitably mixed together at a predetermined ratio and used. The compound content of the plasticizer is 10 to 70 percent by mass, and more preferably 20 to 50 percent by mass, based on the total amount of the base.

Examples of the tackifier of component 6) include petroleum resin, a rosin resin, hydrogenated rosin, ester gum, terpene resin, modified terpene resin, aromatic hydrocarbon resin, aliphatic hydrocarbon resin, and the like. Only one type of tackifier may be used or two or more types of tackifiers may be suitably mixed together at a predetermined ratio and used. The compound content of the tackifier is 5 to 50 percent by mass, and more preferably 10 to 30 percent by mass, based on the total amount of the base.

The support member used in the pharmaceutical composition of the present invention in a form of adhesive preparation is not particularly limited, and a common material can be used for the support member of the adhesive preparation. For example, the support member way be a natural or synthetic polymer woven fabric, non-woven fabric, sheet, film, or a laminated body thereof. Preferable examples of the synthetic polymer include polyvinylchloride resin, a polyethylene resin (such as polyethylene resin or a blend of polyethylene resin and another resin), an ethylene copolymer (such as a copolymer of ethylene and another monomer), a polypropylene resin (such as polypropylene resin or a blend of polypropylene resin and another resin), polyurethane resin, and the like. The size, shape, thickness and the like of the support member is suitably selected.

The liner used in the pharmaceutical composition of the present invention in a form of adhesive preparation is not particularly limited, and a common material can be used for the liner of the adhesive preparation. For example, the liner may be a natural or synthetic polymer sheet, film, or a laminated body thereof. Preferable examples of the liner include release paper that has been treated (synthetic polymer coated, for example) to facilitate release, and sheets, films, or a laminated body thereof, of cellophane, polyethylene, polyethylene terephthalate, polypropylene, polyester, polyvinylidene chloride.

In the pharmaceutical composition of the present invention, in addition to the base and the active ingredient being 3-methyl-1-phenyl-2-pyrazolin-5-one or a medically acceptable salt thereof, various agents commonly used in conventional percutaneous absorption preparations can be blended together at predetermined ratios as necessary. Some of these various agents include a percutaneous absorption accelerator, a tackifier, a softener, an antioxidant, an age resistor, a preservative, an aromatizing agent, a pH adjuster, an emulsifying agent, a dispersing agent, a stabilizing agent, an antiseptic agent, a diluting agent, and a dissolving agent.

The active ingredient 3-methyl-1-phenyl-2-pyrazolin-5-one or a medically acceptable salt thereof is highly reactive because it has a free radical eliminating function. As a result, its stability is poor. In an injectable solution, the number of base components is low so the stability of the active ingredient when used in an injectable solution is good. In a percutaneous absorption type pharmaceutical composition, however, other additives are often added in addition to the essential components during manufacturing. Therefore, when the active ingredient is used in the pharmaceutical composition, the stability of the active ingredient decreases depending on the formula. In this case, adding an antioxidant as a stabilizing agent is effective to stabilize the product.

Examples of the antioxidant include ascorbic acid, palmitic acid, sodium hydrogensulfite, sodium edetate, tetrasodium edetate, dried sodium sulfite, citric acid, sodium citrate, tocopherol acetate, dl-α-tocopherol, potassium dichloro isocyanurate, dibutyl hydroxytoluene, butylhydroxyanisol, soybean lecithin, sodium pyrosulfite, 1, 3-butylene glycol, benzotriazole, penta-erythryl-tetrakis [3-(3,5-di-tertiery butyl-4-hydroxyphenyl)propionate], propyl gallate, 2-mercaptobenzimidazole, and the like. Only one type of the antioxidant may be used or two or more types of antioxidants may be suitably mixed together at a predetermined ratio and used. The compound content of the antioxidant is 0.005 to 20 percent by mass, and preferably 0.1 to 5 percent by mass, based on the total amount of the base.

The percutaneous absorption accelerator is not particularly limited as long as it is one which is normally used in percutaneous absorption preparations. Examples of the percutaneous absorption accelerator include alcohol, fatty acid, fatty acid ester, fatty acid ether, lactic acid ester, acetic acid ester, terpene compound, pyrrolidone derivative, organic acid, organic acid ester, essential oil, hydrocarbon, azone or a derivative thereof, and the like. More specifically, the percutaneous absorption accelerator is ethanol, oleyl alcohol, lauryl alcohol, myristyl alcohol, cetyl alcohol, crotamiton, cyclodextrin, calcium thioglycolate, N-methyl-2-pyrrolidone, ethyl lactate, cetyl lactate, lactic acid, urea, 1-menthol, mentha oil, d-limonene, dl-camphor, or the like. Only one type of percutaneous absorption accelerator may be used or two or more types of percutaneous absorption accelerators may be suitably mixed together at a predetermined ratio and used. The compound content of the percutaneous absorption accelerator is 0.1 to 20 percent by mass, and preferably 0.1 to 5 percent by mass, based on the total amount of the base.

Examples of the dissolving agent include n-methyl-2-pyrrolidone, crotamiton, macrogol, isopropanol, mentha oil, propylene glycol, butylene glycol, oleyl alcohol, isopropyl myristate, and the like. In particular, n-methyl-2-pyrrolidone and crotamiton are effective as dissolving agents due to the high solubility of 3-methyl-1-phenyl-2-pyrazolin-5-one.

In addition, in order to stabilize 3-methyl-1-phenyl-2-pyrazolin-5-one which is the active ingredient of the present invention, in the packaging of the preparation with a packaging material such as aluminum, polyester, polypropylene or the like, it is effective to enclose a deoxidant together or substitute by inert gas such as nitrogen or the like in the package.

EXAMPLES

The present invention will be described more specifically according to the following examples to which the present invention is not limited.

Example 1

Liquid A was adjusted by mixing 5 parts of sodium polyacrylate, 6 parts of starch acrylate, 9 parts of talc and 35 parts of concentrated glycerin. Liquid B was adjusted by dissolving 2.3 parts of tartaric acid in 21.5 parts of water. Liquid C was adjusted by dissolving 3 parts of 3-methyl-1-phenyl-2-pyrazolin-5-one in 5 parts of lactic acid, 5 parts of isopropanol, 1 part of isopropyl myristate, 1 part of 1-menthol and 0.4 part of Polysorbate 80. Liquid B and liquid C were added to liquid A. Also, 2.5 parts of polyacrylate copolymer emulsion and 0.2 part of aluminum hydroxide gel suspended in 3.1 parts of water were added and mixed homogeneously to obtain a mixture. This mixture was spread on a polyester non-woven fabric, and then covered with a polyethylene film. This was then cut into predetermined dimensions to obtain a percutaneous absorption preparation containing 3-methyl-1-phenyl-2-pyrazolin-5-one.

Control 1

Liquid A was adjusted by mixing 5 parts of sodium polyacrylate, 6 parts of starch acrylate, 12 parts of talc, and 35 parts of concentrated glycerin. Liquid B was adjusted by dissolving 2.3 parts of tartaric acid in 21.5 parts of water. Liquid C was adjusted by dissolving 1 part of 1-menthol in 5 parts of lactic acid, 5 parts of isopropanol, 1 part of isopropyl myristate and 0.4 part of Polysorbate 80. Liquid B and Liquid C were added to liquid A. Also, 2.5 parts of polyacrylate copolymer emulsion and 0.2 part of aluminum hydroxide gel suspended in 3.1 parts of water were added and mixed homogeneously to obtain a mixture. This mixture was spread on a polyester non-woven fabric, and then covered with a polyethylene film. This was then cut into predetermined dimensions to obtain a control (a percutaneous absorption preparation containing no active ingredient and consisting of only a base).

Test Example 1

In Vivo Rat Patch Test
Test Method

In a test group, under ether anesthesia, the hair on the abdomens of rats (Crj;CD(SD), male, 8-week-old) was shaved off, and the percutaneous absorption preparation of Example 1 of 20 $cm^2$ skin was applied on the rat abdomens, thereafter covered with a stretch bandage. The preparation was peeled off after 24 hours. In a control group, Radicut Injection (containing 3-methyl-1-phenyl-2-pyrazolin-5-one in 30 mg/20 ml) was administered to a rat identical with the above from tail vein (3 mg/kg in the term of 3-methyl-1-phenyl-2-pyrazolin-5-one). From rats of both groups, bloods were collected at a time intervals, and the concentration of 3-methyl-1-phenyl-2-pyrazolin-5-one in the plasma was determined with HPLC.

Results

The results are shown in FIG. 1. FIG. 1 is a graph showing the concentration in the plasma of 3-methyl-1-phenyl-2-pyrazolin-5-one in the test group and control group on the lapse of time.

As clear from FIG. 1, in a case where the percutaneous absorption preparation of Example 1 was applied, the concentration of drug in the plasma exceeds the level of intravenous administration 2 hours after application, and thereafter was able to be maintained at a general constant concentration of drug in the plasma until after 24 hours when the preparation was peeled off. On the contrary, in a case where Radicut Injection was administered, a high concentration of drug in the plasma was shown immediately after intravenous injection, but it was rapidly reduced, and disappeared after 4 hours.

Consequently. the area under the concentration of drug in the plasma (AUC) in the percutaneous absorption preparation of Example 1 clearly exceeds AUC of the dose (3 mg/kg in the term of 3-methyl-1-phenyl-2-pyrazolin-5-one) of Radica Injection that is regarded as an amount sufficient for developing beneficial effect in animals, and thereby it is understood that the preparation of Example 1 is a useful preparation.

Test Example 2

Beneficial Effect and Pharmacological Test With Rat-Transient Focal Cerebral Ischemia Model
Test Method After introducing an anesthesia by inhalation of 2% influrane (anesthesia background; laughing gas:oxygen=7:3) to rats (Crj:CD(SD), male, 8-week-old), the rats were fixed on their back, and the anesthesia was maintained with 2% influrane.

In order to control the body temperature during surgery, a prove for temperature (Yokogawa Electric Corporation, Digital Thermometer IM 2455) was inserted in the rectum, the change of the body temperature before and after was monitored. When a lowering in the body temperature was detected, the body temperature was maintained near 37° C. by use of an incandescent lamp. The right common carotid artery and external carotid were exposed, and the common carotid artery and external carotid were ligated with a structure (No. 5) in order to close the middle cerebral artery, and No. 4 Nylon tread (a plug) that was preliminary coated with silicone (xanthopren L, Heraeus Kulzer Japan Co., Ltd.) and cut in a length of 19 mm was inserted from a branched part of the external carotid and the internal carotid to close the middle cerebral artery. After 2 hours of the closure of the middle cerebral artery, the plug was pulled out, the blood flow of the middle cerebral artery was restored. Immediately after the restoration of the blood flow, the percutaneous absorption preparation of Example 1 (20 cm$^2$) was applied on the abdomens that was preliminarily coat-cut with a hair clipper and a shaver and coated with a stretch bandage.

To a control group, a base (20 cm$^2$) of Control 1 was applied similarly. After 24 hours of the restoration of the blood flow, the animals were decapitated, and the whole brains were removed quickly. Brain slices having a thickness of 2 mm were prepared with a tissue chopper (Micro-3D, The Micle Laboratory Engineering Co., Ltd.). The brain slices were cut out from the parts from which a crown face of 4 mm anterior to Bregma, 2 mm anterior to Bregma, on Bregma, 2 mm posterior to Bregma and 4 mm posterior to Bregma. The brain slices were immersed and stained in a solution of 1 w/v % 2,3,5-triphenyltetrazolium chloride (TTC) at room temperature, and photographed. The obtained photograph was subjected to image analysis (Adobe Photoshop 3.0J; Adobe Systems Incorporated, Color Count 0.3b; K&M Software Corporation), and the area of cerebral infarction was determined as an observed value.

Figure 2:
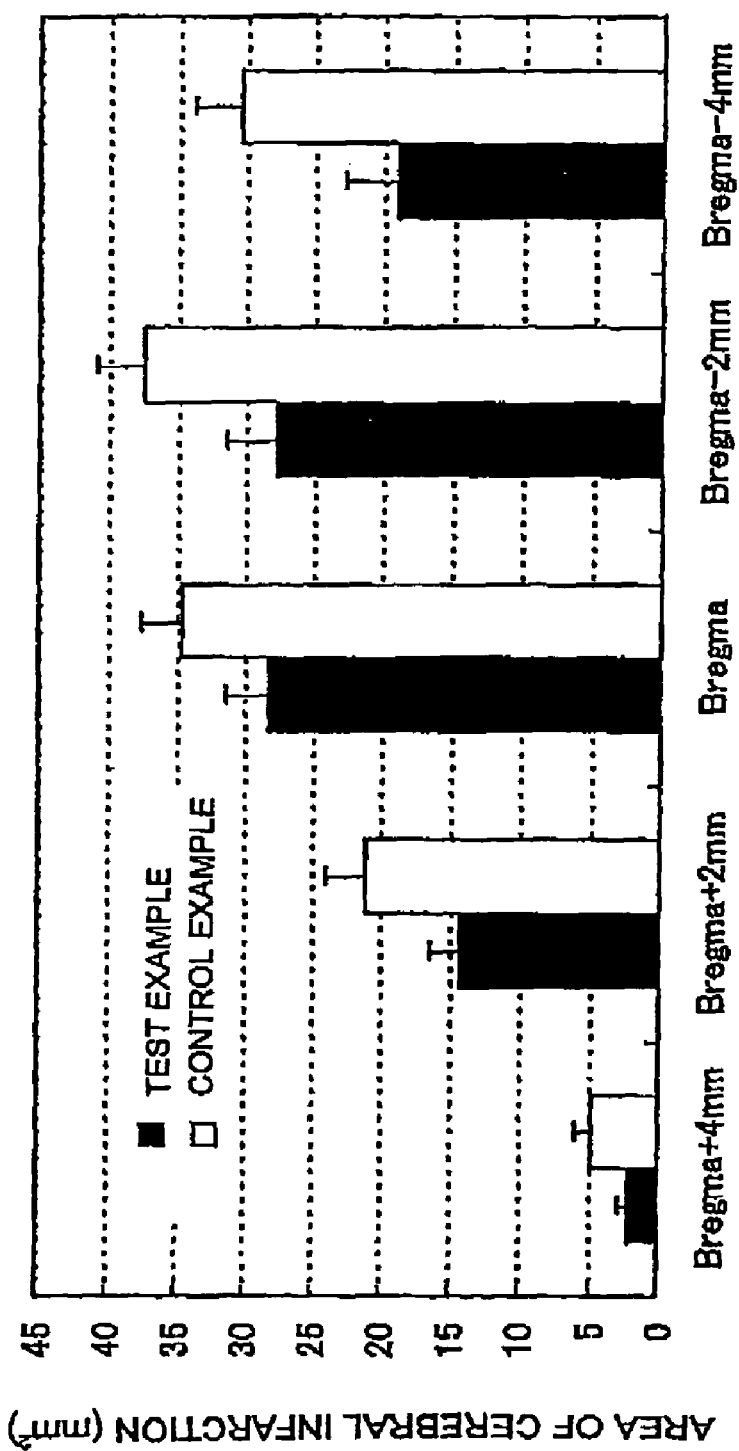
FIG. 2 is a graph showing the area of cerebral infarction in a rat-transient focal cerebral ischemia model in a case where the percutaneous absorption preparation of Example 1 has been applied to a rat or in a case where only a base has been applied to a rat.

Results
The results are shown in FIG. 2 and TABLE 1

TABLE 1

Effect of percutaneous absorption preparation of Example 1 in rat transient focal cerebral ischemia model

| Group | Number of Animals | Area of Cerebral Infarction (mm$^2$) | | | | |
|---|---|---|---|---|---|---|
| | | Bregma + 4 | Bregma + 2 | Bregma | Bregma − 2 | Bregma − 4 |
| Test Group | 12 | 2.2 ± 0.7 | 14.3 ± 2.1 | 28.3 ± 3.1 | 27.8 ± 3.5 | 30.4 ± 3.4* |
| Control Group | 12 | 4.8 ± 1.3 | 21.0 ± 2.9 | 34.6 ± 3.0 | 37.4 ± 3.5 | 19.0 ± 3.8 |

*p < 0.05, Significant difference with the control group is confirmed.

As clear from FIG. 2 and TABLE 1, the percutaneous absorption preparation of Example 1 was significantly reduced in the area of cerebral infarction (p<0.05, 4 mm posterior to Bregma) compared with the control group, and showed cerebral protective effect.

In the meantime, in a case where 3-methyl-1-phenyl-2-pyrazolin-5-one being the active ingredient of the present invention was intravenously administered two times (immediately after restoration of blood flow and 30 minutes after the restoration thereof) in an amount of 3 mg/kg as an injectable solution to a transient focal cerebral infarction model of the same test system, the area of cerebral infarction was almost same as that of the control group, and thereby clear effect was not shown. It is assumed that this contributes to transient change of blood concentration in case where an injection was administered, as shown in Test Example 1. On the contrary, in a case where a percutaneous absorption type is used as in the present invention, it is assumed that a prolonged blood concentration of the active ingredient was reflected to the effects. Therefore, it can be said that a percutaneous absorption preparation is a useful preparation type in case where a drug disappears rapidly from blood.

INDUSTRIAL APPLICABILITY

In the present invention, 3-methyl-1-methyl-2-pyrazolin-5-one being an active ingredient can be easily administered to human, and an effective concentration is maintained over an extended period of time. Therefore, the present invention can inhibit effectively and over an extended period of time, cerebral cell death that occurs following ischemia. In addition, as the preparation of the present invention is percutaneous absorption type one, it does not cause the patient pain or restrict the patient for a certain period of time during use as does the conventional injectable solution (intravenous drip infusion).

Accordingly, the present invention is useful for inhibiting cell death that occurs following ischemia due to causes such as cerebral infarction or the like, particularly for inhibiting cerebral cell death.

The invention claimed is:
1. A method of protecting against cerebral dysfunction, comprising:
 administering to a patient in need of protecting against cerebral dysfunction a percutaneous absorption type pharmaceutical composition that comprises, as an active ingredient, 3-methyl-1-phenyl-2-pyrazolin-5-one represented by the following formula:

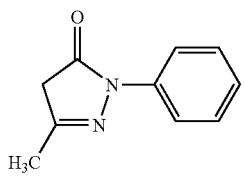

or a medically acceptable salt thereof,
the active ingredient being present in an amount of 0.5 to 10 percent by mass in an aqueous base, the aqueous base comprising, based on a total amount of the aqueous base:
1 to 20 percent by mass of a water-soluble polymer,
0.01 to 20 percent by mass of a cross-linking agent,
10 to 80 percent by mass of polyhydric alcohol, and
1 to 80 percent by mass of water,
wherein the percutaneous absorption type pharmaceutical composition further comprises one or more of talc, lactic acid, isopropanol and polysorbate 80.

2. The method according to claim 1, wherein the percutaneous absorption type pharmaceutical composition further comprises n-methyl-2-pyrrolidone or crotamiton as a dissolving agent.

3. The method according to claim 1, wherein the percutaneous absorption type pharmaceutical composition further comprises tartaric acid as a speed adjuster.

4. The method according to claim 2, wherein the percutaneous absorption type pharmaceutical composition further comprises tartaric acid as a speed adjuster.

5. The method according to claim 2, wherein the dissolving agent is crotamiton.

6. The method according to claim 5, wherein the percutaneous absorption type pharmaceutical composition further comprises tartaric acid as a speed adjuster.

7. The method according to claim 1, wherein the percutaneous absorption type pharmaceutical composition comprises talc.

8. The method according to claim 1, wherein the percutaneous absorption type pharmaceutical composition comprises lactic acid.

9. The method according to claim 1, wherein the percutaneous absorption type pharmaceutical composition comprises isopropanol.

10. The method according to claim 1, wherein the percutaneous absorption type pharmaceutical composition comprises polysorbate 80.

11. The method according to claim 1, wherein the percutaneous absorption type pharmaceutical composition further comprises talc, lactic acid, isopropanol and polysorbate 80.

12. The method according to claim 1, wherein the percutaneous absorption type pharmaceutical composition comprises 5 parts of sodium polyacrylate, 6 parts of starch acrylate, 9 parts of talc, 35 parts of concentrated glycerin, 2.3 parts of tartaric acid, 24.6 parts of water, 3 parts of 3-methyl-1-phenyl-2-pyrazolin-5-one, 5 parts of lactic acid, 5 parts of isopropanol, 1 part of isopropyl myristate, 1 part of 1-menthol, 0.4 part of Polysorbate 80, 2.5 parts of polyacrylate copolymer emulsion, and 0.2 part of aluminum hydroxide gel.

* * * * *